(12) United States Patent
Pageard

(10) Patent No.: US 9,743,973 B2
(45) Date of Patent: *Aug. 29, 2017

(54) TRIPLE BALLOON CATHETER

(71) Applicant: Medtronic CryoCath LP, Toronto (CA)

(72) Inventor: Jean-Luc Pageard, Montreal (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 449 days.

This patent is subject to a terminal disclaimer.

(21) Appl. No.: 14/564,907

(22) Filed: Dec. 9, 2014

(65) Prior Publication Data

US 2015/0094701 A1   Apr. 2, 2015

Related U.S. Application Data

(62) Division of application No. 12/695,423, filed on Jan. 28, 2010, now Pat. No. 8,926,602.

(51) Int. Cl.
*A61B 18/02* (2006.01)
*A61B 18/00* (2006.01)

(52) U.S. Cl.
CPC ...... *A61B 18/02* (2013.01); *A61B 2018/0022* (2013.01); *A61B 2018/00255* (2013.01);
(Continued)

(58) Field of Classification Search
CPC .. A61B 2018/0022; A61B 2018/00255; A61B 2018/00261; A61B 2018/00375;
(Continued)

(56) References Cited

U.S. PATENT DOCUMENTS 5,472,441 A   12/1995   Edwards et al.
5,536,252 A   7/1996   Imran et al.
(Continued)

FOREIGN PATENT DOCUMENTS

CA   2666334 A1   3/2003
NO   2005065563 A1   7/2005
(Continued)

OTHER PUBLICATIONS

Supplementary European Search Report dated Nov. 15, 2016, for corresponding European Application No. 11 73 6555; filed Jul. 27, 2012 consisting of 8 pages.

*Primary Examiner* — Daniel Fowler
(74) *Attorney, Agent, or Firm* — Christopher & Weisberg, P.A.

(57) ABSTRACT

The present invention advantageously provides a method and system for cryogenically ablating large areas of tissue within the left atrium. In an exemplary embodiment a cryotherapy device includes a catheter body, a proximal end and a distal end; a first lumen; a second lumen; and an ablation element expandable from a first diameter to a second diameter, the ablation element having a surface portion that conforms to the uneven surface topography of the cardiac tissue. The ablation element can include one or more deformable balloon and/or flexible elements. The surface of the balloon can further be shaped by regulation of pressure within the one or more balloons. In an exemplary method, a tissue ablation device is provided and tissue in the left atrium is ablated with the device, whereby the ablation is created by freezing tissue.

16 Claims, 12 Drawing Sheets

(52) U.S. Cl.
CPC .............. *A61B 2018/00261* (2013.01); *A61B 2018/00375* (2013.01); *A61B 2018/00577* (2013.01); *A61B 2018/0212* (2013.01)

(58) Field of Classification Search
CPC .. A61B 2018/0212; A61B 2018/00166; A61B 2018/025; A61B 2018/0262; A61B 2018/00577
See application file for complete search history.

(56) References Cited

U.S. PATENT DOCUMENTS

| | | |
|---|---|---|
| 5,584,803 A | 12/1996 | Stevens et al. |
| 5,682,906 A | 11/1997 | Sterman et al. |
| 5,725,523 A | 3/1998 | Mueller |
| 5,752,526 A | 5/1998 | Cosgrove |
| 5,820,595 A | 10/1998 | Parodi |
| 5,855,614 A | 1/1999 | Stevens et al. |
| 5,924,424 A | 7/1999 | Stevens et al. |
| 5,971,979 A | 10/1999 | Joye et al. |
| 6,161,543 A | 12/2000 | Cox et al. |
| 6,164,283 A | 12/2000 | Lesh |
| 6,199,556 B1 | 3/2001 | Benetti et al. |
| 6,258,087 B1 | 7/2001 | Edwards et al. |
| 6,283,127 B1 | 9/2001 | Sternman et al. |
| 6,283,959 B1 | 9/2001 | Lalonde et al. |
| 6,290,696 B1 | 9/2001 | Lafontaine |
| 6,401,720 B1 | 6/2002 | Stevens et al. |
| 6,502,576 B1 | 1/2003 | Lesh |
| 6,508,784 B1 | 1/2003 | Shu |
| 6,540,744 B2 | 4/2003 | Hassett et al. |
| 6,585,733 B2 | 7/2003 | Wellman |
| 6,602,276 B2 | 8/2003 | Dobak, III et al. |
| 6,605,056 B2 | 8/2003 | Eidenschink et al. |
| 6,638,237 B1 | 10/2003 | Guiles et al. |
| 6,648,878 B2 | 11/2003 | Lafontaine |
| 6,651,670 B2 | 11/2003 | Rapacki et al. |
| 6,651,671 B1 | 11/2003 | Donlon et al. |
| 6,656,174 B1 | 12/2003 | Hegde et al. |
| 6,672,312 B2 | 1/2004 | Acker |
| 6,679,268 B2 | 1/2004 | Stevens et al. |
| 6,685,732 B2 | 2/2004 | Kramer |
| 6,689,128 B2 | 2/2004 | Sliwa, Jr. et al. |
| 6,736,774 B2 | 5/2004 | Benetti et al. |
| 6,743,225 B2 | 6/2004 | Sanchez et al. |
| 6,755,822 B2 | 6/2004 | Reu et al. |
| 6,758,847 B2 | 7/2004 | Maguire |
| 6,760,620 B2 | 7/2004 | Groenewegen |
| 6,817,999 B2 | 11/2004 | Berube et al. |
| 6,893,436 B2 | 5/2005 | Woodward et al. |
| 6,929,639 B2 | 8/2005 | Lafontaine |
| 6,949,095 B2 | 9/2005 | Vaska et al. |
| 6,955,173 B2 | 10/2005 | Lesh |
| 7,137,395 B2 | 11/2006 | Fried et al. |
| 7,226,446 B1 | 6/2007 | Mody et al. |
| 2002/0007180 A1 | 1/2002 | Wittenberger et al. |
| 2002/0017306 A1 | 2/2002 | Cox et al. |
| 2002/0087151 A1 | 7/2002 | Mody et al. |
| 2002/0169489 A1 | 11/2002 | Dobak, III et al. |
| 2003/0060820 A1 | 3/2003 | Maguire et al. |
| 2003/0125721 A1 | 7/2003 | Yon et al. |
| 2004/0073301 A1 | 4/2004 | Donlon et al. |
| 2004/0225342 A1 | 11/2004 | Callister |
| 2005/0010201 A1 | 1/2005 | Abboud et al. |
| 2005/0182395 A1 | 8/2005 | Lafontaine |
| 2006/0116701 A1 | 6/2006 | Crow |
| 2006/0212027 A1 | 9/2006 | Marrouche et al. |
| 2006/0247611 A1 | 11/2006 | Abboud et al. |
| 2008/0243111 A1 | 10/2008 | Gammie et al. |

FOREIGN PATENT DOCUMENTS

| | | |
|---|---|---|
| WO | 0007657 A1 | 2/2000 |
| WO | 0200128 A2 | 1/2002 |
| WO | 0207628 A2 | 1/2002 |
| WO | 02083196 A2 | 10/2002 |
| WO | 03020334 A2 | 3/2003 |
| WO | 2005065562 A1 | 7/2005 |
| WO | 2005089853 A1 | 9/2005 |

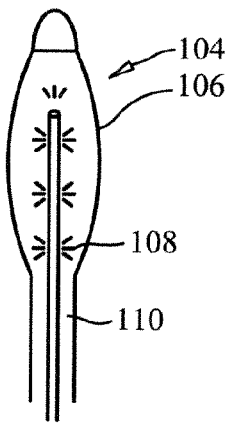
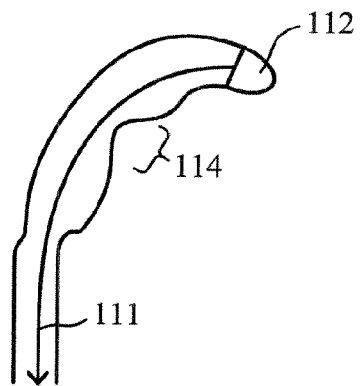
*Fig. 12*  *Fig. 13*
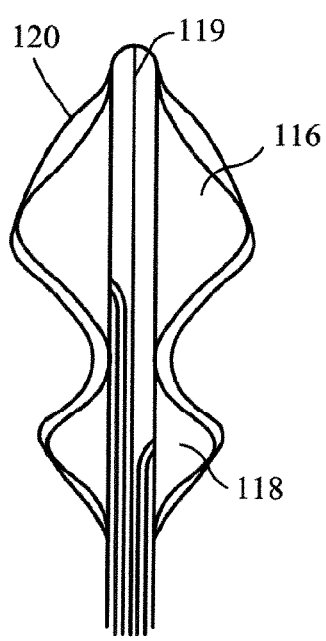
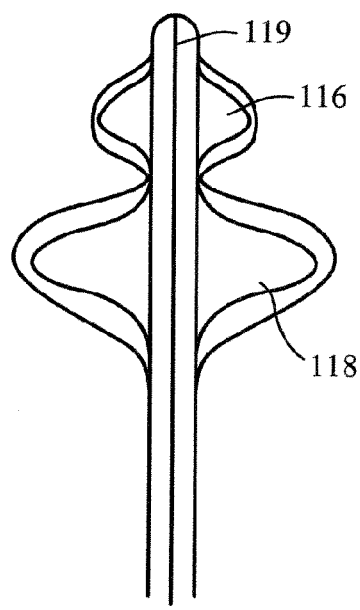
*Fig. 14a*  *Fig. 14b*

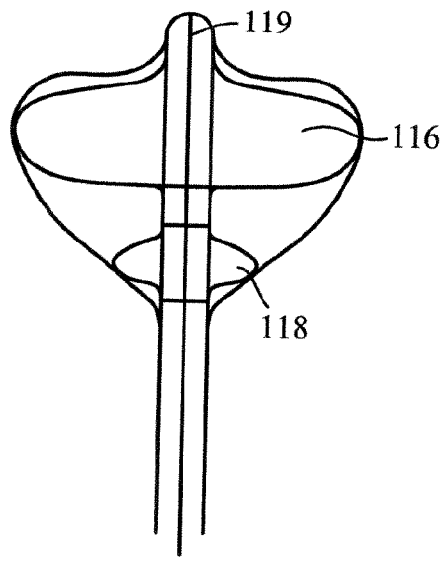 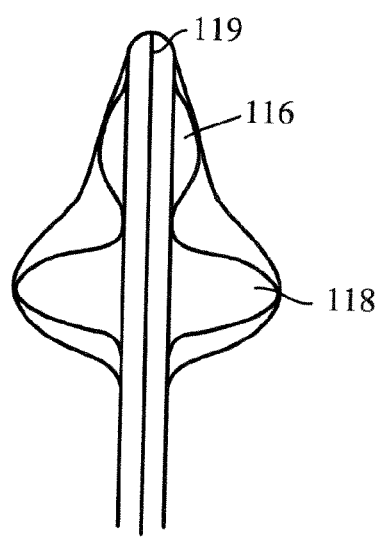
Fig. 15              Fig. 16
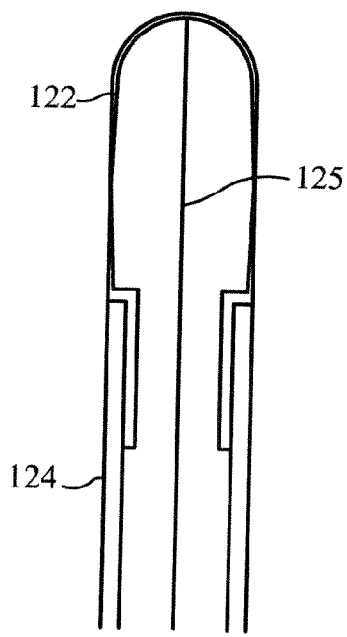 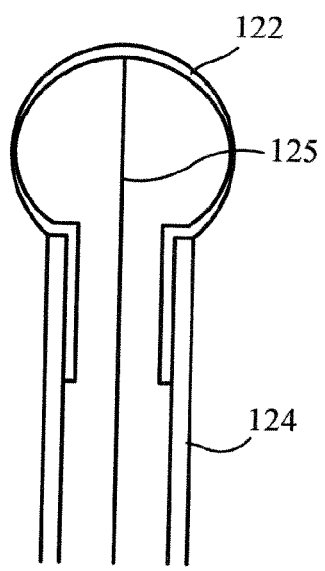
Fig. 18              Fig. 19

TRIPLE BALLOON CATHETER

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method and system for interventional electrophysiology and minimally invasive cardiovascular treatment.

BACKGROUND OF THE INVENTION

Minimally invasive surgical techniques are known for performing medical procedures within all parts of the cardio-vascular system. Exemplary known procedures include the steps of passing a small diameter, highly-flexible catheter through one or more blood vessels and into the heart. When positioned as desired, additional features of the catheter are used, in conjunction with associated equipment, to perform all or a portion of a medical treatment, such as vessel occlusion, tissue biopsy, or tissue ablation, among others. Almost always, these procedures are performed while the heart is beating and blood is flowing. Not surprisingly, even though visualization and positioning aids are adequate for general placement of the device, maintaining the device in a selected position and orientation can be difficult as the tissue moves and blood flows, especially during a procedure that must be done quickly. As diagnostic and visualization equipment and techniques have continued to evolve, it has become possible to identify tissue areas to be treated with greater precision than the ability to quickly situate the device and effectuate treatment.

In addition to the challenges presented by moving tissue and flowing blood, the actual topography of the tissue being treated presents challenges. For example, unlike stylized drawings that depict the interior of the chambers of the heart as having smooth, evenly curved walls leading neatly to tubular blood vessels, the interior surfaces of the heart's chambers are irregular, uneven, and fibrous, as are the openings to blood vessels. Thus, for procedures that call for uniform tissue contact or tissue contact along an extended line, the structure and techniques for use of known devices can be deficient in some regards.

Even if a device is capable of being properly placed and held in position at the proper orientation; and even if the device is suitable for the tissue topography at the treatment site, the device can be nevertheless not fully suitable to achieve the desired outcome. By way of example, catheter-based devices are known for placement in the left atrium for ablating tissue within the atrium for the purpose of electrically isolating one or more pulmonary veins from the atrium in an attempt to increase the success rate of atrial fibrillation ablation.

In one type of prior art device disclosed in U.S. Patent Publication 2002/012836 A1, and as shown in FIG. 1 (prior art), a sheath or guide catheter 10 is inserted into a blood vessel 12 that leads to the right atrium 14 of the heart 16 and passed through an opening created in the septum 18 that separates the right and left atria into the left atrium 20. As shown in FIG. 2 (prior art), a treatment element 22 is passed through the guide catheter 10, deployed from an opening in the distal end thereof, and caused to form a substantially circular loop that is traverse or perpendicular to the longitudinal axis of the guide catheter 10. A distal tip element 24 that extends distally beyond the circular loop is inserted into a pulmonary vein 26 as a guide and placement aid for the loop. As shown in FIG. 3 (prior art), the treatment element 22 in the form of a loop is placed so that it encircles the opening or entry of the pulmonary vein 26, known as the ostium, and tissue is ablated by microwave heating of the contacted tissue. The intended result is a substantially uniform circle of ablated tissue 28 as shown in FIG. 4 (prior art). Also as shown in FIG. 4 (prior art), such a device can be used in an attempt to create linear lesions 30 and 32 as well.

In practice, uniform, unbroken lesion lines are hard to create with such loop shaped ablation elements. Also, with respect to both the circular and the linear lesions formed by microwave ablation, it should be noted that the lesion formed is relatively narrow and has a width that corresponds to about the width of the catheter. Devices that use a laser to ablate tissue provide a similar result; namely, a very narrow lesion. Further, because a laser ablates a very narrow line of tissue, precise alignment of the device is very important. However, for the reasons set forth above, such precision is very difficult to achieve.

Catheter-based devices have been introduced that cryogenically ablate tissue. These devices are structurally very different from RF catheter based devices, and they are not similar or comparable variations on the same theme. Not only are the structures that encompass the respective ablation technologies different, but so are the devices for controlling the ablation process, evaluating the progress and extent of ablation, and ensuring patient safety.

For example, to create a large "ring" with an RF catheter it is typically necessary to make a series of adjoining spot lesions of relatively small size using small electrodes if one wishes to minimize RF output. This is significant because use of a large electrode and/or high power output can seriously injure tissue at other than the intended treatment site. This is especially important with respect to creating lesions in the pulmonary veins because the veins are juxtaposed with bronchial tubes and other sensitive pulmonary tissue within which it is highly undesirable to create ancillary lesions. By contrast, cryogenic ablation of tissues does not need to be accomplished "bit by bit" for fear of energy transmission into the affected tissue as the transfer of heat occurs at the medical device.

Nevertheless, given the uneven topography of the tissue, anatomical differences between patients, and the tortuous environment of the blood flowing through the vasculature mentioned above, secure placement of a cryogenic device against a pulmonary vein remains challenging. Moreover, if too much force is applied to the device and thus the tissue, risk of damaging the pulmonary vein increases—e.g., the vein could be deformed, ruptured, stenosed, or otherwise injured. In view of the above, it would be desirable to provide a medical device and treatment methods of use thereof that allow for secure placement against uneven, topographical surfaces such as those found in the left atrium of the heart while reducing or otherwise minimizing the risk of unwanted injury to the tissue region being treated.

SUMMARY OF THE INVENTION

The present invention advantageously provides a method and system for cryogenically ablating large areas of tissue within the left atrium. In particular, the present invention advantageously provides a medical device and treatment methods of use thereof that allow for secure placement against uneven, topographical surfaces such as those found in the left atrium of the heart while reducing or otherwise minimizing the risk of unwanted injury to the tissue region being treated.

In an exemplary embodiment a cryotherapy device is provided for modifying the electrophysiological properties of cardiac tissue having an uneven surface topography, wherein the device includes a catheter body having a substantially fixed diameter, a proximal end and a distal end; a first lumen for permitting passage of a cooling fluid from the proximal end to the distal end; a second lumen permitting return of the cooling fluid from the distal end to the proximal end; and an ablation element expandable from a first diameter that is substantially the same as the diameter of the catheter body to a second diameter that is at least twice the diameter of the catheter body, the ablation element having a surface portion that conforms to the uneven surface topography of the cardiac tissue. The ablation element can include one or more balloons and/or a flexible element that is deformed by moving the distal end of the catheter toward the proximal end of the catheter. The surface of the balloon can further be shaped by regulation of pressure within the one or more balloons.

The invention also includes a method for modifying the electrophysiological properties of cardiac tissue wherein a tissue ablation device is provided and tissue in the antrum of the left atrium is ablated with the device. In an exemplary method, only tissue in the antrum is ablated, and the ablation is created by freezing tissue. In addition, an exemplary method of a cryomaze procedure is provided which can be performed without the need to arrest the heart of the patient.

A cryogenic device is also provided, including a first substantially non-compliant balloon; a second substantially compliant balloon positioned distal to the first balloon; and a third substantially compliant balloon surrounding the first and second balloons. The first balloon may be constructed from PET, nylon or similar polymeric materials or composites, and the second balloon may be constructed from polyurethane, latex, or similar polymeric materials or composites. The first balloon may have an elastic modulus between approximately 2700 MPa and approximately 4250 MPa, while the second balloon may have an elastic modulus between approximately 50 MPa and approximately 600 MPa. The first and second balloons may be expandable independently of one another, and may not be in fluid communication with each other. The device may also include a cryogenic fluid supply in fluid communication with the first balloon, and a non-cryogenic fluid in fluid communication with the second balloon. Further, an interstitial region may be defined between the third balloon and at least one of the first and second balloons; and a vacuum source can be placed in fluid communication with the interstitial region.

A medical system is also provided, having a flexible catheter body; a first balloon disposed on the catheter body; a second balloon disposed distally of the first balloon, wherein the second balloon is more readily deformable than the first balloon; and a third balloon substantially enclosing the first and second balloons to the define an interstitial region therebetween.

A method for treating cardiac tissue is also provided, including positioning a medical device proximate an ostium such that a first balloon of the medical device abuts cardiac tissue proximate to the ostium and at least a portion of a second balloon located distal to the first balloon is positioned within the ostium, where the first and second balloons are substantially enveloped within a third balloon; expanding the second balloon to substantially occlude the ostium; and ablating cardiac tissue with at least one of the first and second balloons. Expanding the second balloon may include partially inflating the second balloon to substantially less than its maximum volume or diameter. The first balloon may define an elastic modulus at least five times greater than an elastic modulus defined by the second balloon.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 12 depicts the ablation element of FIG. 10 in a partially inflated state suitable for deflection;

FIG. 13 depicts the ablation element of FIG. 10 in the partially inflated state shown in FIG. 12 being deflected to a curved configuration;

FIG. 14a shows yet another embodiment of the ablation element;

FIGS. 14b-16 illustrate the ablation element in exemplary deployment configurations;

FIG. 17b shows an exemplary use of the ablation element of FIG. 17a;

FIG. 18 illustrates yet another embodiment of an ablation element;

FIG. 19 shows the ablation element of FIG. 18 in a deflected condition;

DETAILED DESCRIPTION OF THE INVENTION

With respect to the treatment of atrial fibrillation, it is believed that the creation of a conduction block or an interruption of the electrical signal flow path from the region of the atrium and the pulmonary vein is an effective treatment for atrial fibrillation. Further, while it is believed that the creation of a narrow annular lesion at or very near the ostium of the pulmonary vein is an effective way to create a conduction block, notwithstanding the difficulty of making such a lesion, it is believed that creating one or more non-annular lesions in different locations is not only more readily accomplished with reliability, but it is more clinically effective.

In view of the preceding, the present invention provides apparatus and methods for modifying the electrophysiological properties of large areas of tissue rather than narrow, annular lesions at locations that are not confined solely to the ostium, although ablation of tissue near the ostium and/or in the atrial wall may be included. More particularly, the present invention provides devices that are suitable to cryogenically ablate regions of tissue in the antrum region of the left atrium in addition to other atrial tissue that may be deemed to be arrhythmogenic. The antrum is the area between the mouth or ostium of a pulmonary vein and the atrium. The antrum of each pulmonary vein is not identical in size or shape and the tissue topography renders it very difficult or almost impossible to create a ring of tissue. Accordingly, the present method calls for ablating large regions of tissue in the antrum to render the tissue electrically dysfunctional.

Figure 1:
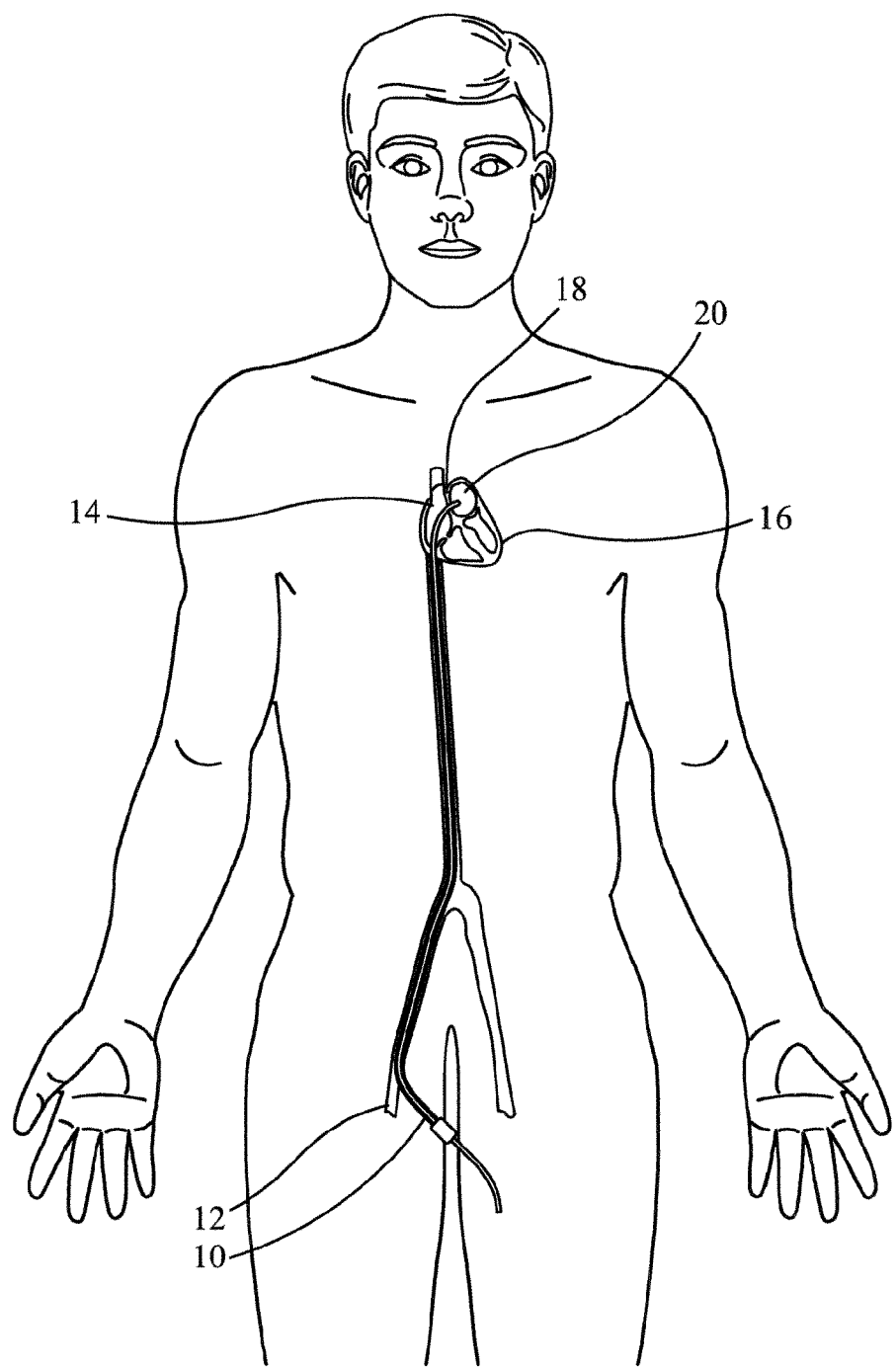
FIG. 1 depicts a prior art technique for placing a distal portion of a medical device within the heart.
Figure 3:
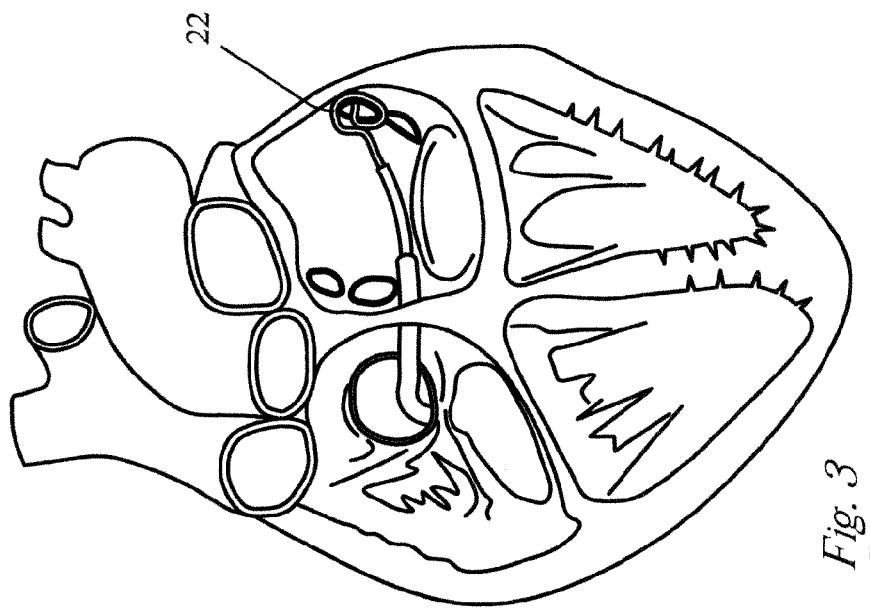
FIG. 3 depicts a prior art technique for creating a lesion with a prior art microwave ablation device.
Figure 2:
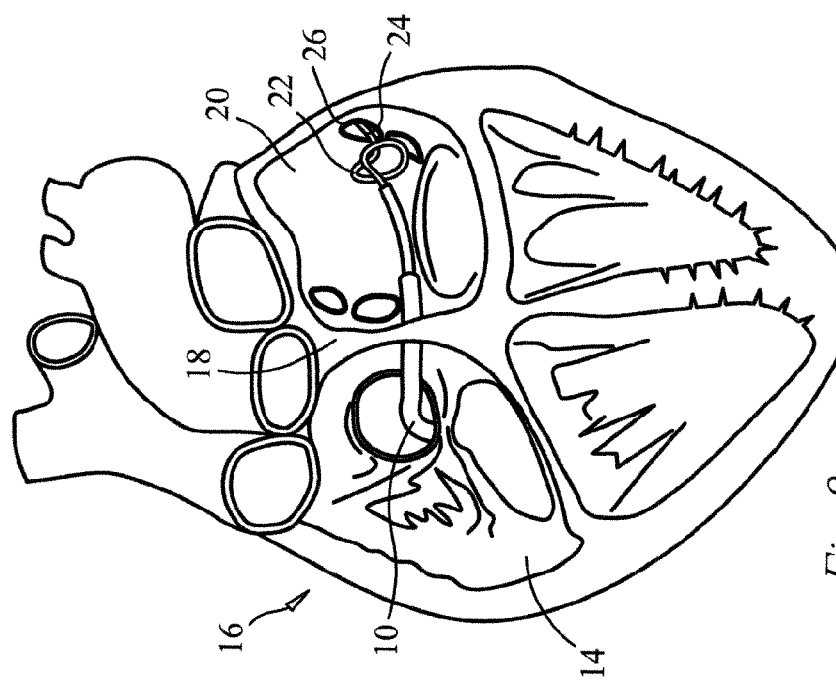
FIG. 2 illustrates a prior art technique for positioning a prior art device within the left atrium.
Figure 4:
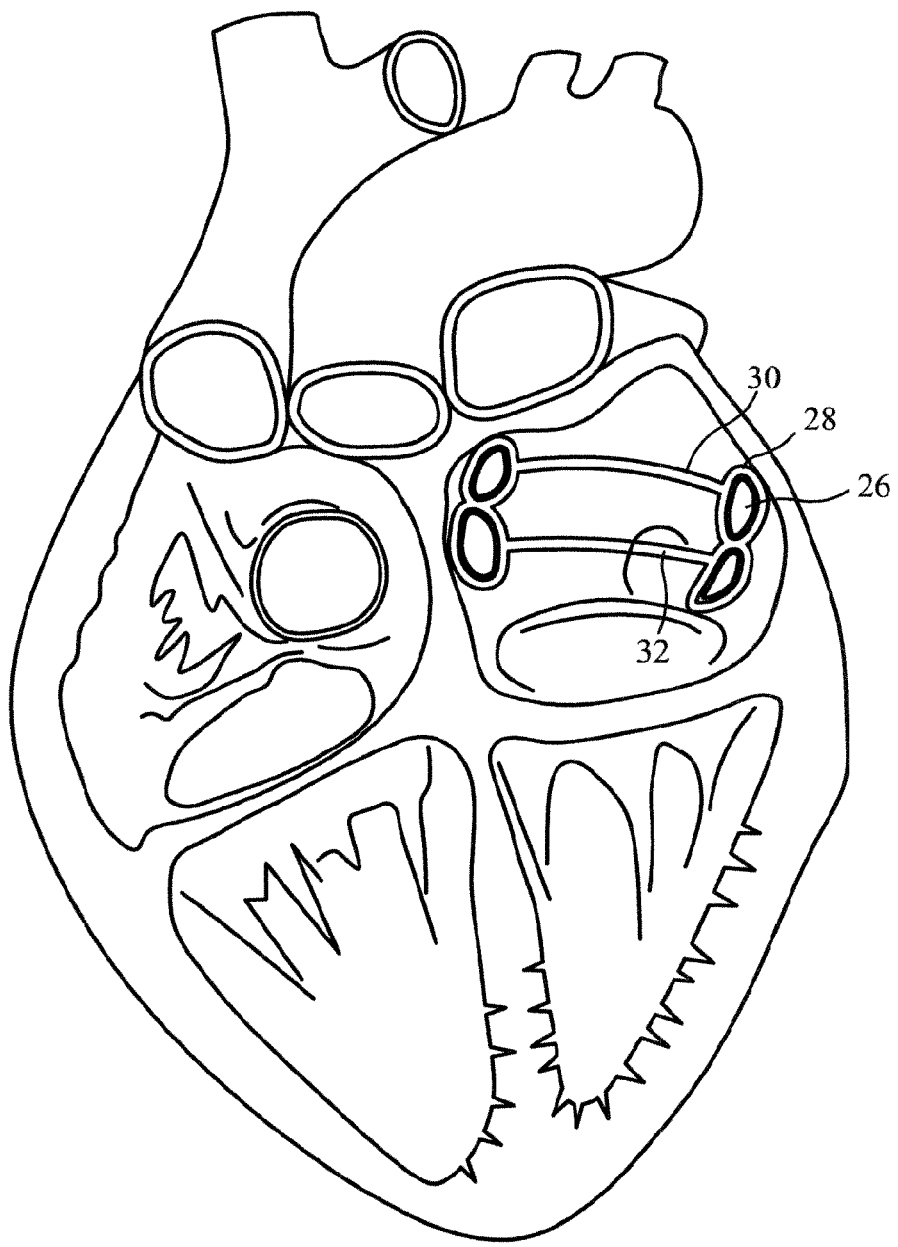
FIG. 4 shows lesions formed using the prior art techniques and devices of FIGS. 1, 2 and 3.
Figure 5:
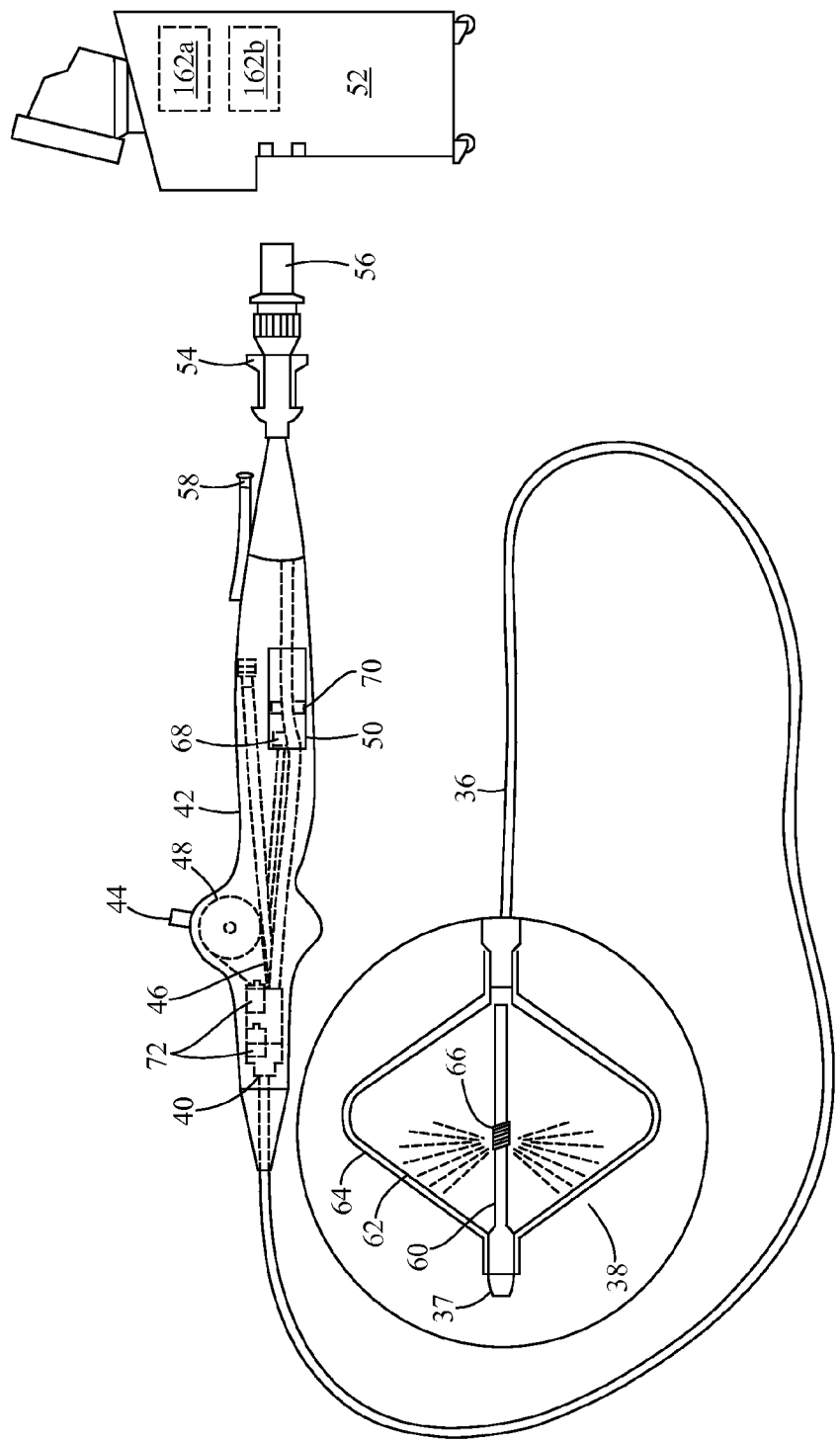
FIG. 5 is a schematic illustration of a cryogenic ablation system in accordance with the present invention.

Referring now to FIG. 5, an exemplary system is depicted that is suitable for performing cryogenic antral ablation. The system generally includes a medical device, which may include an elongate, highly flexible ablation catheter 34 that is suitable for passage through the vasculature. The ablation catheter 34 includes a catheter body 36 having a distal end 37 with an ablation element 38 at or proximal to the distal end. The distal end 37 and the ablation element 38 are shown magnified and are described in greater detail below. The ablation catheter 34 has a proximal end 40 that is mated to a handle 42 that can include an element such as a lever 44 or knob for manipulating the catheter body 36 and the ablation element 38. In the exemplary embodiment, a pull wire 46 having a proximal end and a distal end has its distal end is anchored to the catheter at or near the distal end 37. The proximal end of the pull wire is anchored to an element such as a cam 48 in communication with and responsive to the lever 44. The handle 42 can further include circuitry 50 for identification and/or use in controlling of the ablation catheter or another component of the system.

Continuing to refer to FIG. 5, the handle 42 can also include connectors that are matable directly to a cryogenic fluid supply/exhaust and control unit or indirectly by way of one or more umbilicals. In the system illustrated, the handle 42 is provided with a first connector 54 that is matable with a co-axial fluid umbilical (not shown) and a second connector 56 that is matable with an electrical umbilical (not shown) that can further include an accessory box (not shown). In the exemplary system the fluid supply and exhaust, as well as various control mechanisms for the system are housed in a single console 52. In addition to providing an exhaust function for the ablation catheter fluid supply, the console can also recover and/or recirculate the cooling fluid. The handle 42 is provided with a fitting 58 for receiving a guide wire (not shown) that is passed into a guide wire lumen 60.

Still referring to FIG. 5, the ablation element 38 is shown as a double balloon, wherein an inner balloon 62 is contained by an outer balloon 64. A coolant supply tube 66 in fluid communication with the coolant supply in the console 52 is provided to release coolant from one or more openings in the tube within the inner balloon 62 in response to console commands and other control input. A vacuum pump in the console 52 creates a low pressure environment in one or more lumens within the catheter body 36 so that coolant is drawn into the lumen(s), away from the inner balloon, and toward the proximal end of the catheter body. The vacuum pump is also in fluid communication with the interface of the inner and the outer balloons so that any fluid that leaks from the inner balloon is contained and aspirated. Still referring to FIG. 5, the handle includes one or more pressure sensors 68 to monitor the fluid pressure within one or both of the balloons, blood detection devices 70 and pressure relief valves 72. When coolant is released into the inner balloon 62, the inner and the outer balloon 64 expand to a predetermined shape to present an ablation surface, wherein the temperature of the ablation surface is determined by the material properties of the specific coolant selected for use, such as nitrous oxide, along with the pressure within the inner balloon and the coolant flow rate.

Figures 6, 7:
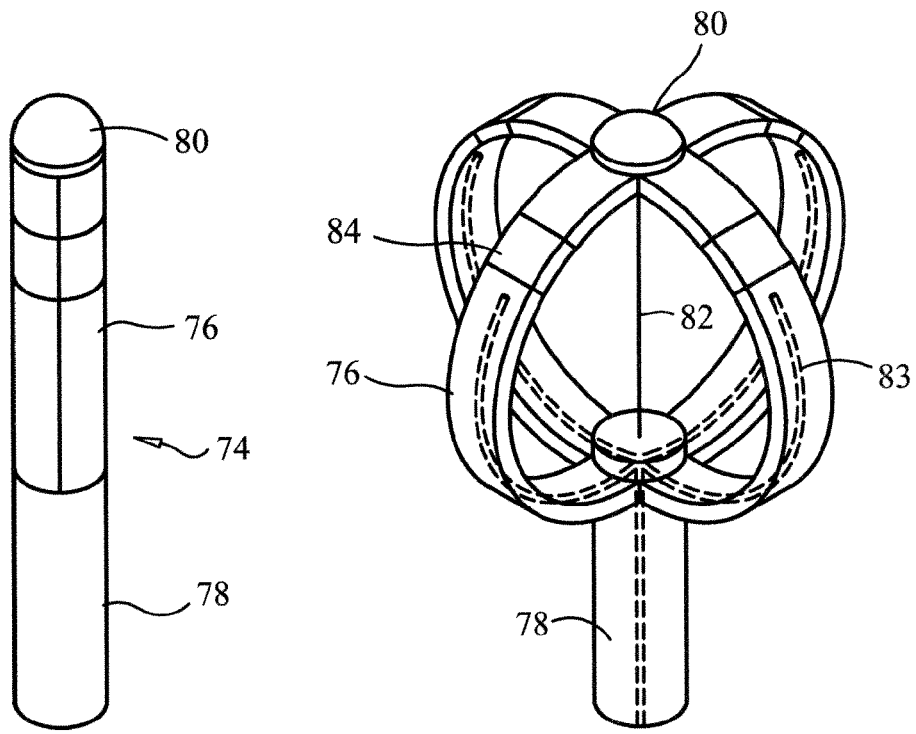
FIG. 6 is a side view of an exemplary ablation element for the system of FIG. 5.
FIG. 7 depicts the ablation element of FIG. 6 is an expanded state.

Although the double balloon type ablation element 38 illustrated in FIG. 5 can be an effective ablation tool, FIGS. 6-20 illustrate other configurations for the ablation element that are capable of creating wide-area ablation patterns. For example, as shown in FIG. 6, a distal catheter portion 74 includes longitudinal elements 76 secured to a main catheter body 78 proximally, and to a tip element 80, distally. A pull wire 82 or pushrod connected to a manipulation element 44 at the proximal end of the catheter and to the tip element 80 is movable longitudinally to move the tip element longitudinally. Electrodes 84 can be associated with one or more of the longitudinal elements for use in monitoring or evaluating electrical activity in tissue.

As shown in FIG. 7, the pull wire 82 has been pulled proximally to draw the tip element 80 toward the catheter body 78. This causes the longitudinal elements 76 to deform and bend or bow radially outward. In one embodiment, each of the longitudinal elements 76 are provided with coolant injection tubes 83 disposed within a lumen defined by each longitudinal element, wherein coolant is recovered in the lumen which is in fluid communication with a low pressure source. Thus, each of the longitudinal elements 76 are cooled. Although the injection tubes 83 can all be supplied with coolant simultaneously, if desired, less than all of the injection tubes can be supplied with coolant to provide selectively radial cooling.

Figure 8:
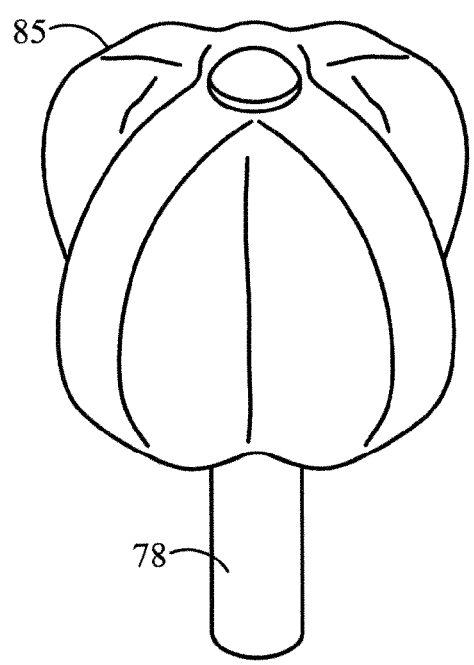
FIG. 8 shows an alternative embodiment of the ablation element of FIG. 6, wherein a membrane is disposed over expansion elements positioned in an expanded state.

As shown in FIG. 8, the longitudinal elements can support a single or a double layer flexible member 85 that envelops them. Instead of, or in addition to coolant being circulated through the longitudinal members as discussed with respect to FIG. 7, coolant can be circulated through the chamber defined by the elements and the flexible member as described with respect to FIG. 5 and the pull wire 82 can be used to deform the balloon by moving the distal end of the device proximally and distally.

Figure 9:
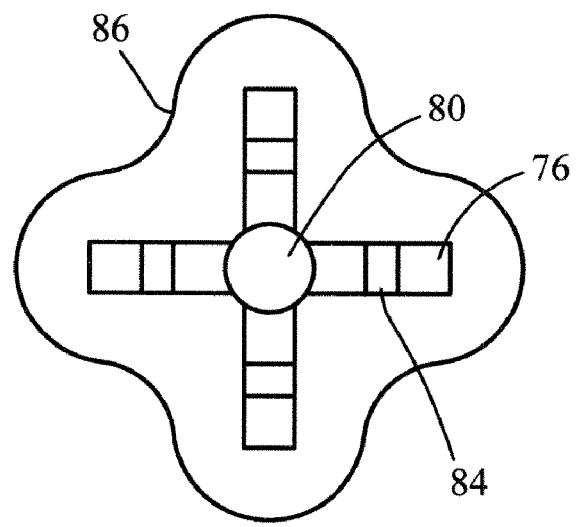
FIG. 9 is a front view of the ablation element of FIG. 6, wherein an ablation pattern created by the device is shown.

FIG. 9 is a front view of the device of FIGS. 7 and 8 and it illustrates the general shape of the periphery 86 of a lesion formed by cryoablation using the exemplary device in the expanded state. By contrast, spot or linear lesions can be created when the distal catheter portion 74 is in the non-expanded state illustrated in FIG. 6.

Figure 10:
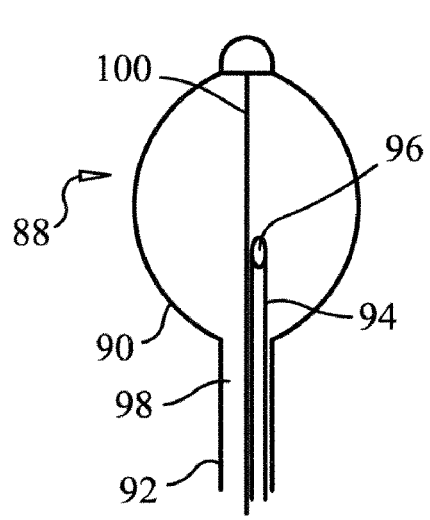
FIG. 10 illustrates an alternative embodiment for the ablation element in a partially expanded state.
Figure 11:
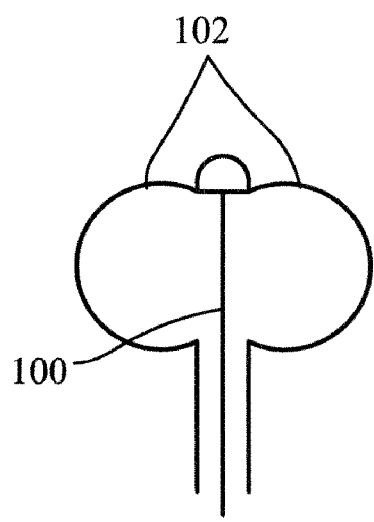
FIG. 11 illustrates the ablation element of FIG. 10 in a fully expanded state.

Referring now to FIG. 10, a catheter is provided with an ablation element 88 similar to the double balloon structure of FIG. 5 so that a distal tip region 90 is radially expandable to at least double the diameter of a catheter body 92 over a 2*cm* to 3*cm* length. The ablation element 88 is provided with a cryogenic fluid injection tube 94 having one or more fluid outlets 96 along its length in the distal tip region. Coolant is withdrawn though an outer lumen 98 at reduced pressure. A pull wire 100 or pushrod is used to deflect the distal catheter portion as shown in FIG. 11 so that a large, distal facing surface 102 can be placed into contact with tissue. Although the balloon when inflated as shown in FIG. 10 has a substantially greater radius than the catheter body 92, when the pull wire 100 is used to draw the distal tip toward the catheter body as shown in FIG. 11, the balloon expands even further and presents a flattened tip that is suitable to blot large areas of tissue.

Referring now to FIG. 12, an ablation element 104 is provided with a distal portion 106 that is inflatable, one or more coolant injection orifices 108 and an exhaust lumen 110. Referring to FIG. 13, the ablation element 104 is shown with a pull wire 111 or pushrod connected to a manipulation element at the proximal end of the catheter and the tip element 12 so as to be movable longitudinally to deflect the tip element off axis. In addition to providing a relatively long and wide ablation surface, the ablation element can be provided with a notch 114 to accommodate or fit over a ridge of tissue.

FIGS. 14*a*-16 illustrate an embodiment for an ablation element, wherein first and second balloons, 116 and 118, respectively, are enveloped by a third balloon 120. The first and the second balloons 116 and 118 are in fluid communication with inflation and exhaust lumens as described above, wherein the third balloon 120 is only in communication with a vacuum or low pressure source. Each of the first and second balloons may be provided with a predetermined or substantially preformed shape or dimension and/or may be pressurized or otherwise inflated to provide an overall surface topography for the ablation element. Additional shaping may be provided by manipulation of a pull wire 119 as described above or by regulation of the pressure in the exhaust flow path.

Figure 17A:
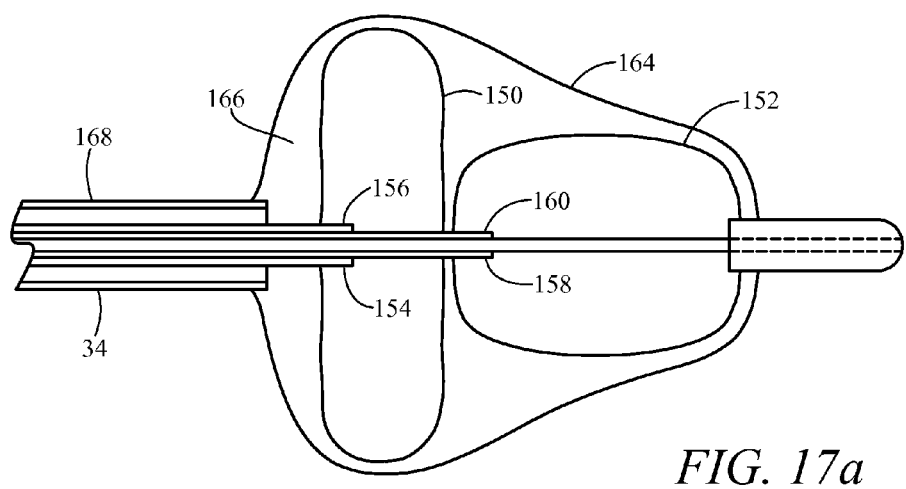
FIG. 17a shows yet another embodiment of the ablation element.

FIG. 17*a* provides an additional illustration of a triple-balloon configuration of the catheter 34 for the medical system. In particular, a first balloon 150 may be disposed on the elongate body of the catheter 34. The first balloon 150 may be substantially non-compliant when in an inflated state. For example, the first balloon 150 may be constructed from polyethylene terephthalate ("PET"), nylon or similar polymeric materials or composites. Located distally of the first balloon 150 on the catheter 34 may be a substantially compliant, second balloon 152. The second balloon 152 may be constructed from polyurethane, latex, or similar polymeric materials or composites. The substantially increased elasticity or compliance of the second balloon 152 as compared to the first balloon 150 may result in the second balloon 152 being more readily deformable than the first balloon 150 when inflated and/or in contact with a targeted tissue area. To facilitate the desired conformity or lack thereof, the first balloon may have an elastic modulus approximately five to fifty times that of the second balloon. For example, the first balloon may define an elastic modulus between approximately 2700 MPa and approximately 4250 MPa, while the second balloon may have an elastic modulus between approximately 50 MPa and approximately 600 MPa The first and second balloons 150, 152 may be inflatable and/or otherwise operable independently from one another. For example, the interior of the first balloon 150 may be in fluid communication with a first inflation lumen 154 and a first exhaust lumen 156. These inflation and exhaust lumens may be in fluid communication with a fluid source and/or vacuum source, respectively, contained within the console 52. The interior of the second balloon 152 may be in fluid communication with a second inflation lumen 158 and a second exhaust lumen 160. The separate fluid flow paths of the first and second balloons enable them to be sealed or otherwise not in fluid communication with each other. These inflation and exhaust lumens may also be in fluid communication with a fluid source and/or vacuum source, respectively, contained within the console 52. Of note, the first and second balloons may be in fluid communication with independent, separated first and second fluid sources 162*a*, 162*b* respectively, (shown in FIG. 5). The first fluid source 162*a* may contain a cryogenic coolant or refrigerant, while the second fluid source 162*b* may contain a non-cryogenic fluid, such as saline, non-cooled gas, or the like.

The catheter 34 shown in FIG. 17*a* may further include a third balloon 164 surrounding, substantially enclosing or otherwise enveloping the first and second balloons. The third balloon 164 may be substantially compliant and be constructed from polyurethane, latex, or similar polymeric materials or composites, having a modulus of elasticity or flexibility substantially larger than that of the first balloon. The third balloon 164 may be disposed about the first and second balloons to define an interstitial region 166 therebetween, which may be in fluid communication with an interstitial lumen 168. The interstitial lumen 168 may be in fluid communication with a vacuum source in the console 52, and which may be the same or additional to the vacuum source(s) in fluid communication with either of the first and second exhaust lumens 156, 160.

Figure 17B:
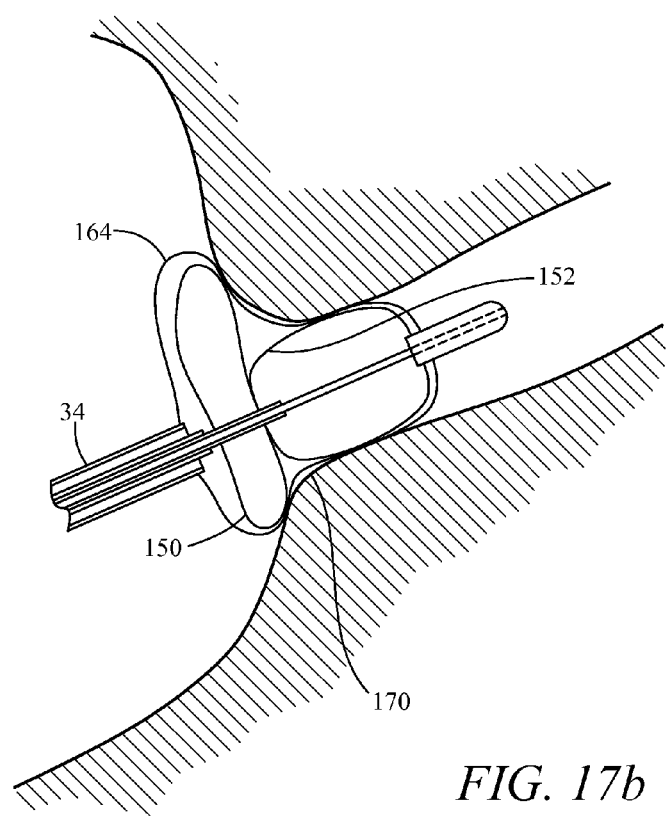

Now referring to FIG. 17*b*, an exemplary method of use of the device shown in FIG. 17*a* is illustrated. In particular, the catheter 34 may be positioned and subsequently operated to thermally treat a targeted tissue area, such as an ostium 170 of a pulmonary vein in the atrium of the heart. For example, the catheter 34 may be delivered to or otherwise positioned within an atrium of a heart intravascularly or otherwise as described herein. The catheter 34 may be positioned such that at least a portion of the second balloon 152 is disposed within a pulmonary vein or other vascular conduit. The second balloon 152 may then be expanded or otherwise inflated to substantially occlude the pulmonary vein or other vessel in which it resides. The expansion of the second balloon 152 may be achieved by delivering a fluid, such as a non-cryogenic fluid, saline, or the like, from the second fluid source 162*b* through the second inflation lumen 154 and into the interior of the balloon 152. Further, as there may be variations in the size, shape or other dimensions of the vessel being occluded, the second balloon 152 may be selectively, controllably expanded to a fraction of its overall inflation/size capacity to obtain the resulting, desired occlusion. This partial inflation may be facilitated by monitoring the pressure within the second balloon and terminating inflation upon reaching a desired or predetermined pressure threshold value or range. Another example of providing a controlled, fractional inflation of the second balloon may include delivering a predetermined volume of inflation medium to the second balloon 152 to reach a predetermined or preselected inflation size (whether volume, outer circumference, diameter, or the like). In addition to the selective inflation dimensions of the second balloon 152, occlusion may further be facilitated by the complaint nature of the second balloon 152, described above. Having a sufficiently-compliant interface with the contacting tissue allows the second balloon 152 to conform to the uneven surface topography of the occluded vessel, resulting in an enhanced, more effective occlusion.

Anchoring and/or sufficiently occluding the targeted vessel with the second balloon 152 further allows positioning the first balloon 150 to abut against a tissue wall or region (such as the atrial wall) surrounding or otherwise extending from the ostium. The first balloon 150 may then be operated to exchange thermal, ablative energy between the balloon 150 and the proximate tissue. In particular, a cryogenic coolant or medium may be circulated through the first balloon 150 via the first inflation and exhaust lumens, 154, 165.

Of course, during the positioning and operation of the first and second balloons, the third balloon 164 surrounds the first and second balloons, thereby providing both a safety barrier in the event of a structural failure of either the first and second balloons, as well as a conformable interface pliably extending between the first and second balloons. The third balloon 164 thus further facilitate occlusion of the ostium, as well as contact with the surrounding tissue wall proximate the first balloon 150. During operation, the interstitial region may be kept under vacuum to minimize any space between the third balloon 164 and the first and second balloons to reduce thermal isolation and thereby increase heat transfer, as well as providing for the removal of any fluid leaking into the interstitial region 166.

Referring now to FIGS. 18 and 19, yet another configuration for an ablation element is shown wherein an ablation element includes an elastically deformable, thermally-transmissive tip element 122 secured to the distal portion of a catheter body 124. When a load is applied to the tip element 122 it deforms. For example, FIG. 19 illustrates the tip element subject to an axial load, such as is encountered when the tip is pressed against tissue. As shown, the distal portion of the tip element 122 presents a wider ablation surface when deflected as compared to the non deflected state. When the load is removed from the tip, it returns to the shape illustrated in FIG. 18. Fluid supply and exhaust lumens are provided as disclosed above. Also as described above, a pull wire 125 can be secured to the tip element 122 to help deform the element so that it doesn't need to be pressed hard against tissue. In an exemplary embodiment the tip element 122 is configured so that it is biased into the shape illustrated in FIG. 18. Proximal tension is applied to the pull wire 125 to deform or aid in deforming the tip element to an expanded configuration as shown in FIG. 19. When proximally directed tension is reduced on the pull wire 125, the biasing force of the tip element causes it to return to the configuration shown in FIG. 18.

Figure 20:
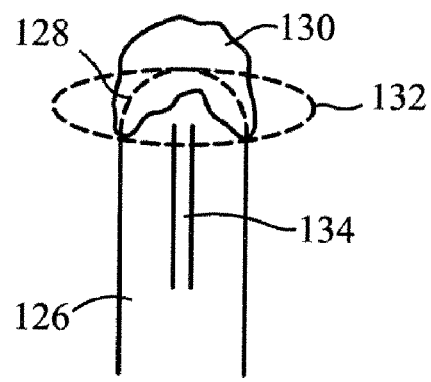
FIG. 20 show yet another ablation element in accordance with the invention.

FIG. 20 illustrates yet another configuration of an ablation element wherein a catheter body 126 has a distal end 128 covered with a mass of thermally conductive, highly elastic material, such as a cohesive gel 130. When the distal end 128 and the gel 130 are pressed against tissue, the gel deforms to provide an enlarged distal end portion as shown by the dashed line 132. Coolant exiting a coolant supply tube 134 cools the distal end 128 and the gel 130.

Figure 21:
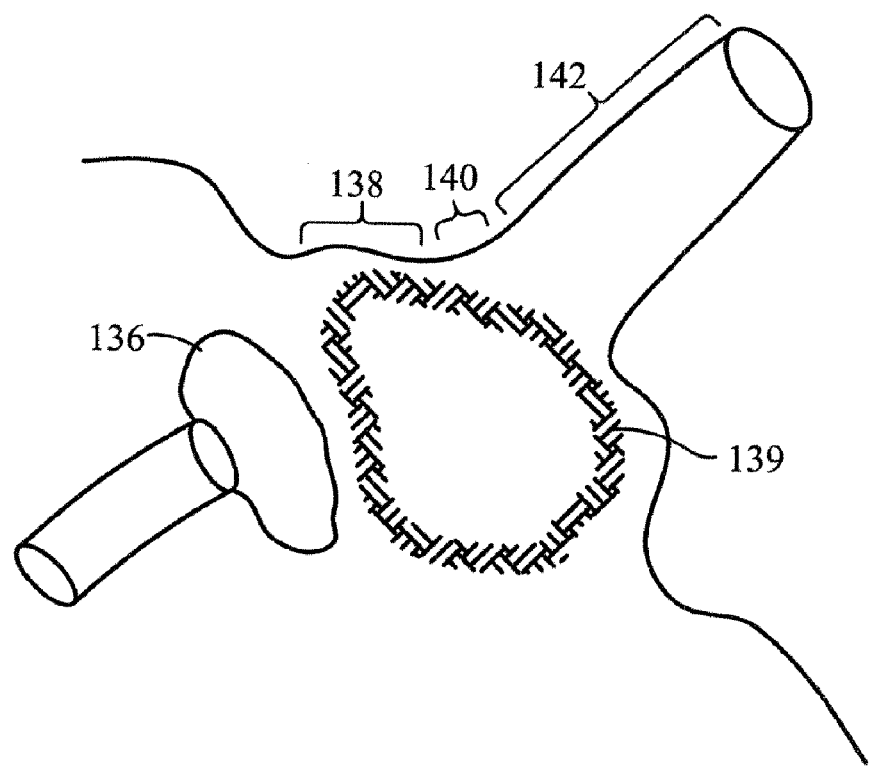
FIG. 21 illustrates an ablation device in accordance with the invention within the left atrium of the heart having created lesions in the left antral region

Turning now to FIG. 21, an exemplary procedure is illustrated wherein an ablation element 136 in accordance with the invention has been delivered transeptally into the left atrium. In the illustration, the ablation element 136 is a balloon that is partially inflated with a nitrous oxide coolant so that it has a "squishy" or highly compliant character and dimensioned so that it can "blot" or contact an area of tissue approximately 28 to 30 mm in diameter. In the exemplary procedure, the balloon is inflated to the desired degree of firmness, or lack thereof, before being advanced toward tissue and the balloon's surface is chilled to a temperature in the range of minus 30 degrees Centigrade to minus 80 degrees Centigrade. The balloon is then placed into contact with tissue in the antrum 138 and the tissue is ablated. The balloon is moved to one or more additional areas of the antrum 138 until the desired tissue modification has been achieved. The balloon can be placed so as to create individual distinct lesions or overlapping lesions. In this fashion, large contiguous lesions can be created. The pattern 139 shown in FIG. 21 illustrates an exemplary lesion periphery created with the ablation element 136.

Because the doctor is not attempting to create a "ring," the balloon does not have to be centered on the ostium 140 and no anchoring is needed. In general, for any of the disclosed cryoablation devices, precise alignment is not as important as with respect to other devices. This is significant, because the precise positioning within the antrum is difficult to achieve. The balloon does not enter the pulmonary vein 142. However, depending upon placement of the balloon, the temperature achieved, and the duration that the balloon is left in place, is possible to ablate tissue in the ostium 140 in addition to tissue within the pulmonary vein 142, as well as the antrum 138.

In another exemplary method, the ablation catheter 34 as described above may be used to create a series of lesions in the heart, whereby the ablation catheter is maneuvered into the left atrium of the heart for treatment of an arrhythmia or other cardiac abnormality. Primarily, the ablation catheter may be positioned in proximity to the heart using one of either a subxyphoid approach, a thoracotomy approach, or a sternotomy method. Each of these methods provides surgical access to the heart for subsequent positioning and insertion into the left atrium of a medical device for ablation of the desired tissue.

Figure 22:
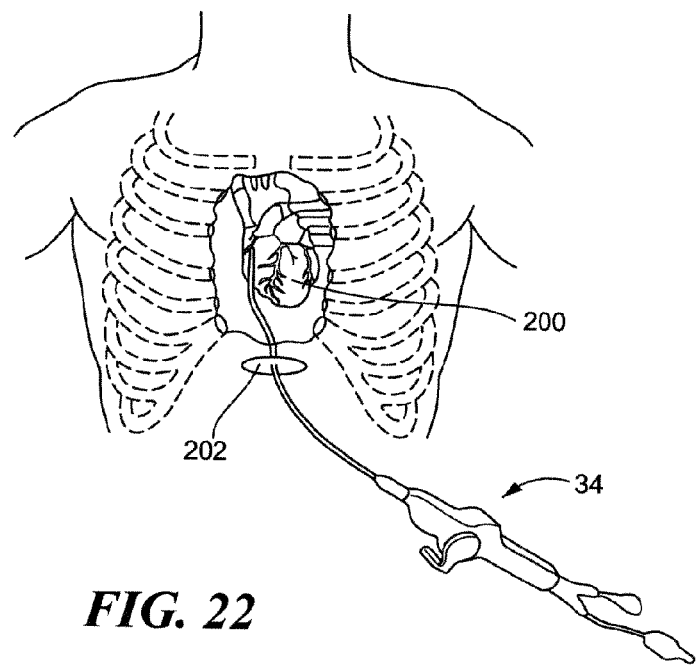
FIG. 22 illustrates a method of use of the present invention.

Now referring to FIG. 22, employing a subxyphoid technique, the heart 200 may initially be accessed through a puncture technique using the same 17-Gauge Tuohy needle that is used to enter the epidural space when administering epidural anesthesia (typically .about.100 mm overall length, and 1.5 mm O.D.). A subxyphoid incision 202, which is typically less than 10 centimeters in length, is created. As the needle approaches the heart 200 under fluoroscopic guidance, small amounts of contrast media are injected to document penetration of the needle tip as it progresses towards the heart. Once properly positioned as indicated by the assistance of medical imaging, a guide wire may be passed through the needle. As a result, a standard introducer sheath, and subsequently an ablation catheter 34, may be passed into a position in proximity to the heart 200.

Figure 23:
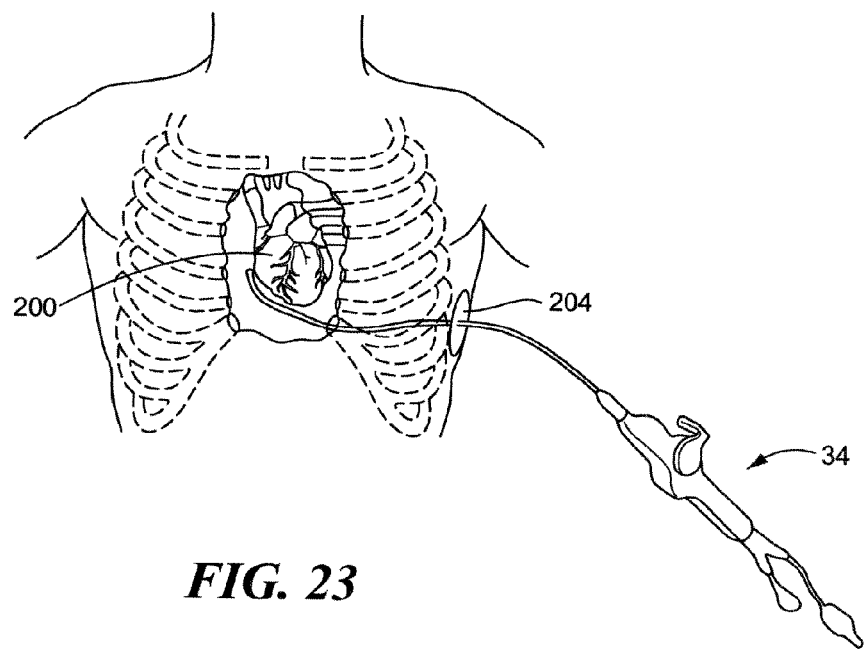
FIG. 23 illustrates an alternative method of use of the present invention.
Figure 24:
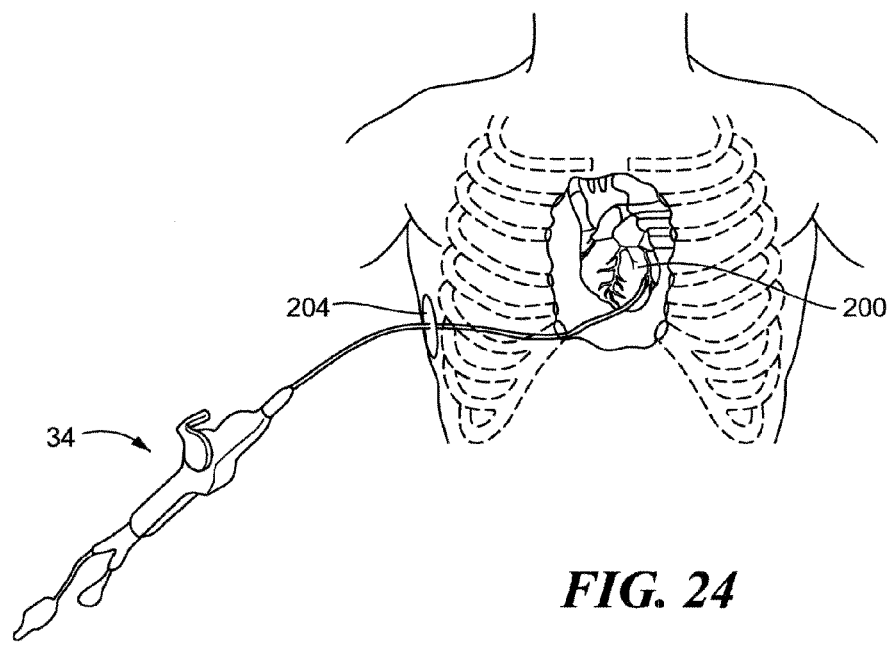
FIG. 24 illustrates another method of use of the present invention.

Now referring to FIGS. 23 and 24, a thoracotomy technique may also be performed for providing initial access the heart 200, whereby one or more small thoracotomy incisions 204 are made in the chest wall between the ribs to permit access for thoracoscopic instruments and cameras, which provide dissection and visualization capabilities in the pericardial space for insertion and manipulation of medical instruments, including the ablation catheter. The small thoracotomy incisions are typically less than 10 centimeters in length. In this approach, the decompression of the pleural space may be necessary in order to achieve pericardial access.

Figure 25:
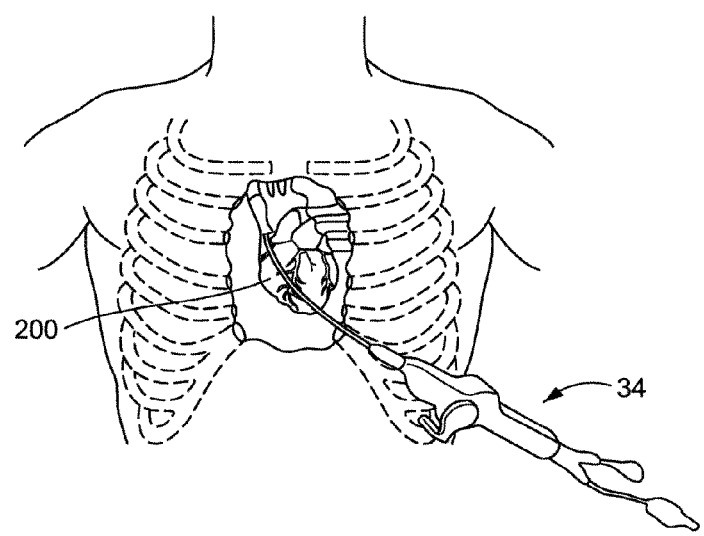
FIG. 25 illustrates an additional method of use of the present invention.

As shown in FIG. 25, a third approach employs a sternotomy, which is commonly performed for open heart surgery, and is the least minimally-invasive of the approaches described above. A full sternotomy may include multiple incisions and the eventual division of the sternum, thereby providing direct access to the heart 200.

Upon generally accessing the heart through any of the above-mentioned approaches, the ablation catheter must further enter the internal chambers of the heart for the eventual ablation of the desired tissue. Such internal access may be achieved by directing the ablation catheter through one of the pulmonary veins or the aorta, through the heart tissue or left atrial appendage, or through the superior vena cava and the septum wall.

To access the internal chambers of the heart through either of the pulmonary veins or the aorta, a pursestring suture may be placed in any of the pulmonary veins or the aorta. Using a seldinger technique, an introducer may be inserted through the pulmonary veins or aorta, and into the left atrium. Once the introducer is appropriately positioned, the ablation catheter may be guided through the introducer and into the left atrium for subsequent ablation of the desired tissue.

Access to the internal chambers of the heart may further be accomplished directly through an exterior surface of the heart, or through the left atrial appendage. For example, a pursestring suture may be placed in the left atrial appendage, through which an introducer and/or guidewire is positioned. As such, the ablation catheter may be guided directly into the left atrium through the left atrial appendage or other exterior heart surface for subsequent ablation of the desired tissue within the heart.

The internal chambers of the heart may additionally be accessed by a transseptal approach. A transseptal approach may include placing a pursestring suture in the lateral wall of the right atrium, providing access for a needle to further be inserted into the heart. The needle, as well as a guidewire and introducer, may be initially guided into the right atrium through the superior vena cava. Further, the needle may be maneuvered through the atrial septum and into the left atrium, at which point the guide wire may be inserted to dilate the opening in the atrial septum. Upon sufficient dilation of the septum, the introducer may be directed through the septum and into the left atrium. Subsequently, the ablation catheter may be guided through the introducer and into the left atrium for ablation of the desired tissue.

Upon accessing the internal chambers of the heart, and more particularly, the left atrium, the ablation catheter can be positioned in the orifice of the right inferior pulmonary vein, possibly employing the aid of fluoroscopy or other medical imaging to facilitate accurate placement of the device. Positioning and occlusion of the vein orifice may further be confirmed through the administration of a contrast dye. Once in the desired location, the ablation catheter can be used to create a lesion around the orifice of the right inferior pulmonary vein. The ablation catheter may then be repositioned in the right superior vein, the left superior vein, and the left inferior pulmonary vein for the creation of additional ablative lesions about the orifices of the respective vessels. An additional lesion may be created to connect the lesions of the left-sided pulmonary veins with the lesions of the right-sided pulmonary veins, to form somewhat of an "eyeglass" pattern.

Upon completion of the creation of the pulmonary vein lesions, one or more lesions, either spot lesions or linear in nature, extending from the left inferior pulmonary vein to the mitral valve annulus can be created using the ablation catheter. In order to confirm that the ablative lesions have in fact been successfully created, a pacing catheter or other electrical-sensing device can be used to monitor electrical pulses in the affected tissue, and ablation may be reinstituted in the desired locations, if necessary. Once the desired portions of the heart have been ablated, the introducer sheath and the ablation catheter can be removed, and the surgical openings may be appropriately closed.

While ablation procedures are typically performed on an arrested heart, the procedure described above may be performed with the ablation catheter on a beating heart employing a thoracoscopic or small thoracotomy approach, which reduces the recovery time for a patient as well as reducing the complexity of the surgical procedure. As such, the higher-risk portions of a typical maze procedure, namely a sternotomy, cardiopulmonary bypass, and/or aortic crossclamping or cardiac arrest, are no longer necessary.

The ablation catheter used to create the lesions described above may include any of the features previously discussed. Moreover, in order to ease the use of the catheter in the transseptal approach, the length of a portion of the catheter may be reduced from that of a standard catheter inserted into the femoral artery or other insertion point distant from the heart. Furthermore, the flexibility of the portions of the catheter may be altered in order to provide increased malleability in order to facilitate the accurate positioning of the ablation element within the heart. Alternatively, pull-wires or other deflection mechanisms can be integrated with or otherwise coupled with the catheter for steering and/or positioning, as is known in the art.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method for treating cardiac tissue, comprising:
positioning a medical device having a longitudinal axis proximate an ostium such that an expanded first balloon of the medical device abuts cardiac tissue proximate to the ostium and at least a portion of an unexpanded second balloon located distal to the first balloon is positioned within the ostium, the first and second balloons being substantially enveloped within a third balloon, each of the first balloon and the second balloon having an anterior face and a posterior face, the anterior face of the first balloon lying in a plane that is at least substantially orthogonal to the longitudinal axis of the medical device, at least a portion of the anterior face of the first balloon being in contact with at least a portion of the posterior face of the second balloon when the first and second balloons are expanded;
expanding the second balloon to substantially occlude the ostium; and
ablating cardiac tissue with at least one of the first and second balloons.

2. The method of claim 1, wherein expanding the second balloon includes partially inflating the second balloon to less than half of its maximum diameter.

3. The method of claim 1, wherein the first balloon has an elastic modulus that is at least five times greater than an elastic modulus of the second balloon.

4. The method of claim 1, wherein the first balloon has an elastic modulus between approximately 2700 MPa and approximately 4250 MPa.

5. The method of claim 4, wherein the second balloon has an elastic modulus between approximately 50 MPa and approximately 600 MPa.

6. The method of claim 1, wherein the third balloon is sufficiently compliant to conform to at least a portion of the anterior face of the first balloon to enhance thermal transfer from the anterior face of the first balloon to the third balloon.

7. The method of claim 1, wherein ablating cardiac tissue includes delivering a cryogenic coolant to the first balloon.

8. The method of claim 1, wherein expanding the second balloon includes delivering a non-cryogenic fluid to the second balloon.

9. The method of claim 1, wherein an interstitial region is defined between the third balloon and at least one of the first and second balloons, further comprising drawing a vacuum on the interstitial region.

10. The method of claim 1, wherein the first balloon is constructed from polyethylene terephthalate or nylon.

11. The method of claim 10, wherein the second balloon is constructed from polyurethane or latex.

12. The method of claim 8, wherein the first balloon and the second balloon are expandable independently of each other.

13. The method of claim 12, wherein the first balloon and the second balloon are not in fluid communication with each other.

14. A method for treating cardiac tissue, the method comprising:
positioning a medical device having a longitudinal axis proximate an ostium such that an expanded first balloon of the medical device abuts cardiac tissue proximate to the ostium and at least a portion of an unexpanded second balloon located distal to the first balloon is positioned within the ostium, the first and second balloons being substantially enveloped within a third balloon, each of the first balloon and the second balloon defining an anterior face and a posterior face, the anterior face of the first balloon lying in a plane that is at least substantially orthogonal to the longitudinal axis of the cryogenic device, at least a portion of the anterior face of the first balloon being in contact with at least a portion of the posterior face of the second balloon when the first and second balloons are expanded;
expanding the second balloon to substantially occlude the ostium; and
ablating cardiac tissue with at least one of the first and second balloons.

15. The method of claim 14, wherein the third balloon is sufficiently compliant to conform to at least a portion of the anterior face of the first balloon to enhance thermal transfer from the anterior face of the first balloon to the third balloon.

16. A method for treating cardiac tissue, the method comprising:
positioning a medical device having a longitudinal axis proximate an ostium such that an expanded first balloon of the medical device abuts cardiac tissue proximate to the ostium and at least a portion of an unexpanded second balloon located distal to the first balloon is positioned within the ostium, wherein the first and second balloons are substantially enveloped within a third balloon, the first balloon defining a posterior face and an anterior face that lies in a plane that is at least substantially orthogonal to the longitudinal axis of the cryogenic device, the second balloon defining a posterior face and an anterior face;
expanding the second balloon to substantially occlude the ostium, at least a portion of the anterior face of the first balloon being in contact with at least a portion of the posterior face of the second balloon when the first balloon and the second balloon are expanded; and
ablating cardiac tissue with at least one of the first and second balloons, the third balloon being sufficiently compliant to conform to at least a portion of the anterior face of the first balloon to enhance thermal transfer from the anterior face of the first balloon to the third balloon.

* * * * *